US008887713B2

(12) United States Patent
Cutts et al.

(10) Patent No.: US 8,887,713 B2
(45) Date of Patent: Nov. 18, 2014

(54) VACCINE NEBULISERS

(71) Applicants: Felicity Cutts, Geneva (CH); Jorge Fernandez De Castro, Santa Maria la Ribera (MX); John V. Bennett, Atlanta, GA (US); Beth Laube, Baltimore, MD (US); Clyde Witham, Saratoga Spring, UT (US); Ana Maria Henao-Restrepo, Geneva (CH); Bernard Cohen, London (GB); David Brown, London (GB); John Dennis, Calgary (CA)

(72) Inventors: Felicity Cutts, Geneva (CH); Jorge Fernandez De Castro, Santa Maria la Ribera (MX); John V. Bennett, Atlanta, GA (US); Beth Laube, Baltimore, MD (US); Clyde Witham, Saratoga Spring, UT (US); Ana Maria Henao-Restrepo, Geneva (CH); Bernard Cohen, London (GB); David Brown, London (GB); John Dennis, Calgary (CA)

(73) Assignee: World Health Organization, Geneva (CH)

( * ) Notice: Subject to any disclaimer, the term of this patent is extended or adjusted under 35 U.S.C. 154(b) by 0 days.

(21) Appl. No.: 13/650,535

(22) Filed: Oct. 12, 2012

(65) Prior Publication Data

US 2013/0032140 A1   Feb. 7, 2013

Related U.S. Application Data

(63) Continuation of application No. 11/993,520, filed as application No. PCT/EP2006/006168 on Jun. 27, 2006, now abandoned.

(30) Foreign Application Priority Data

Jun. 27, 2005   (EP) .................................. 05013805

(51) Int. Cl.
*A61M 11/00* (2006.01)
*A61M 16/10* (2006.01)

(52) U.S. Cl.
CPC ........... *A61M 11/02* (2013.01); *A61M 2202/30* (2013.01); *A61M 15/0086* (2013.01);

(58) Field of Classification Search
CPC .......... A61M 2202/30; A61M 11/001–11/003; A61M 11/005; A61M 11/006; A61M 11/007; A61M 11/02; A61M 11/04; A61M 11/06
USPC ........ 424/184.1; 128/200.16, 203.12, 200.14, 128/200.17, 200.18, 200.21, 200.22, 128/200.23, 200.24, 203.16, 203.26, 203.15
See application file for complete search history.

(56) References Cited

U.S. PATENT DOCUMENTS

| 4,949,715 | A | * | 8/1990 | Brugger | 128/204.21 |
| 6,009,869 | A | * | 1/2000 | Corbeil | 128/200.21 |
| 6,630,169 | B1 | * | 10/2003 | Bot et al. | 424/489 |

(Continued)

*Primary Examiner* — Lynne Anderson
*Assistant Examiner* — Bradley Philips
(74) *Attorney, Agent, or Firm* — Ice Miller LLP (57) ABSTRACT

The invention provides a method of selecting a nebulizer device to be used to deliver a vaccine comprising selecting a nebulizer capable of producing a plurality of vaccine particles having the following particle droplet size distribution:
  (i) $D_{v10}$: 2.0+/−0.2 µm
  (ii) $D_{v50}$: 5.0+/−0.5 µm
  (iii) $D_{v90}$: 10.0+/−1.0 µm
  (iv) a mean mass aerodynamic diameter (MMAD) of 4.5 to 8.0 µm This allows the selection of, for example, commercially available nebulizers, previously used for drug delivery, for vaccine delivery. This considerably reduces the work required to identify suitable nebulizers.
Nebulizers identified by the methods of the invention are also claimed.

27 Claims, 1 Drawing Sheet

(51) Int. Cl.
*A61M 11/02* (2006.01)
*A61M 16/00* (2006.01)
*A61M 15/00* (2006.01)
*A61M 16/06* (2006.01)

(52) U.S. Cl.
CPC ....... *A61M 16/0666* (2013.01); *A61M 16/0045* (2013.01); *A61M 11/005* (2013.01)
USPC .................................. 128/200.14; 128/203.16

(56) References Cited

U.S. PATENT DOCUMENTS 7,452,524 B2 * 11/2008 Hofmann et al. ............... 424/45
2003/0150445 A1 * 8/2003 Power et al. ............. 128/200.14
2005/0112098 A1 * 5/2005 McCray et al. ............. 424/93.2
2006/0292224 A1 * 12/2006 Moore et al. .................. 424/489

* cited by examiner

VACCINE NEBULISERS

CROSS-REFERENCE TO RELATED APPLICATIONS

The present patent application is related to, claims the priority benefit of, and is a continuation application of U.S. Nonprovisional patent application Ser. No. 11/993,520, filed Jan. 26, 2009, which is related to, and claims the priority benefit of PCT application PCT/EP2006/006168, filed Jun. 27, 2006; which is an international application of, and claims priority to European patent application 05013805.6, filed on Jun. 27, 2005. Each of the above-identified applications are now each individually incorporated herein by reference in their entireties.

BACKGROUND

The invention relates to methods of identifying improved vaccine nebulisers and nebulisers comprising those improvements. Vaccines include, but are not limited to measles vaccines. The method allows the rapid identification of nebulisers suitable for testing as vaccine nebulisers via easily testable criteria. It also allows the nebulisers to be optimized for use in the field.

In 2000, WHO (World Health Organization) estimated that there are still 30 million cases of measles each year causing 777,000 deaths. Measles vaccine is highly effective but does not achieve its full potential, in part due to logistical constraints of administering a vaccine by injection to large populations in resource-poor settings. A live attenuated measles vaccine was first developed in the 1960s and has been used ever since, with a reasonable degree of success. Its use has led to an estimated global reduction in measles incidence by about 72% and in measles mortality by 85% (Cutts F. T. et al. Alternative Routes of Immunization: A Review. *Biologicals* (1997), Vol. 25, pages 323-328). However the remaining burden of disease is due to the under-utilisation of the current measles vaccine. Failure to deliver at least one dose of measles vaccine to all infants remains one of the leading causes for the high measles morbidity and mortality that exists today. In addition, a number of safety concerns regarding the use and adequate disposal of syringes and sharps have been documented in a number of countries in recent years.

Delivering the current measles vaccine via the respiratory route might overcome several of the problems. It could be administered by trained lay people and avoids both the spread of blood-borne pathogens and costly disposal of needles and syringes. It would be useful for mass vaccination but also for routine immunization. By potentially reducing the need to use sharps and decreasing recurrent costs, aerosol administration of measles vaccine could make safe measles vaccination more affordable in resource-poor situations.

Respiratory administration of live measles vaccine closely mimics the natural route of measles infection. It is already established that current measles vaccines are more effective or equivalent in inducing antibody production when delivered by nebulisation compared to when delivered parenterally. Maternal antibody interference might be avoided or mucosal immunity might be enhanced. No increase in adverse side effects of respiratory administration has been noted compared to current injection practice.

Clinical studies have been carried out with aerosolized measles vaccines starting in 1983. Almost all of these studies have used the "classic Mexican" device and other variations on the Mexican model.

The classic Mexican prototype device comprised the following components:
1. A car battery or mains electricity powered compressor attached to:
2. A commercially available nebuliser (C4107 from IPI Medical Products, Chicago, USA) attached to a vessel containing measles vaccine. This sat in a vessel of crushed ice.
3. The nebuliser was attached to a flexible Teflon™ tube via a T-piece.
4. The Teflon™ tube comprised a Teflon™ cone with a disposable paper cone as an inset.

No significant increase in adverse events in either recipients or vaccinators have been noted although follow up was sometimes short or not described. Aerosol administration directly compared with subcutaneous injection resulted in fewer reports of adverse events of symptoms of measles disease in the 2 weeks following the vaccination (Sepúlveda-Amor J., et al. A Randomised Trial Demonstrating Successful Boosting Responses Following Simultaneous Aerosols of Measles and Rubella Vaccines in School Age Children. *Vaccine* (2002), Vol. 20, pages 2790-2795; Dilraj A., et al. Response to different Measles Vaccine Strains Given by Aerosol and Subcutaneous Routes to Schoolchildren: a Randomised Trial. *Lancet* (2000a), Vol. 355, pages 798-803). Adverse events assessed included cough, conjunctivitis, rhinitis and sore throat as well as fever, headache and diarrhoea. Rubella vaccine was also studied.

In summary, in children over 9 months old, aerosol administration of EZ strain is the most effective and most extensively tested of all the non-invasive routes of administration. There is some evidence that aerosol administration can evade maternal antibody but it is not clear from the few studies comparing subcutaneous and aerosol EZ in infants less than 9 months old which route is superior (Cutts F. T., et al. (1997) Supra). In this age group there have been some practical difficulties in administration and stable seroconversion was often not established until 3-6 months after vaccination.

Two clinical studies using Serum Institute of India Ltd. (SIIL) E-Z measles-containing vaccines have been carried out in Mexico.

One, using SIIL's combine measles, mumps, rubella vaccine (MMR) was done in 2000 in 100 adults. Aerosol vaccination using the classical Mexican device (50 adults) was compared to the same vaccine given by the currently approved subcutaneous route (50 adults). All subjects were healthy and were tested before the study to show they were measles immune. Differences seen in safety parameters (post auricular swelling and otitis) were likely related to the mumps component. There was a slightly higher rate of lethargy in the aerosol group—but this could be related to any of the three MMR antigens. All other adverse events observed (fever, cough, rhinitis, influenza) were less in the aerosol group than in the s.c. group. A boosting effect was seen in both groups.

A study was carried out in 2002-2003 in Queretaro State, Mexico, using SIIL measles vaccine in infants of approximately 9 months of age with no history of measles disease or measles vaccination. Follow-up and data evaluation have been submitted for publication. The vaccinations were administered to 99 infants, 53 who received measles vaccine by subcutaneous injection and 46 who received measles aerosol vaccination using the classical Mexican device. Results showed that the aerosol group had lower overall seroconversion and lower cell mediated immunity than the subcutaneous group, but the aerosol dose was determined to be more than 10 fold lower in the aerosol group (2.81 logs vs 4.28 logs). The investigators considered this to be the reason for the lower response by aerosol. However, among those children that developed a measles-specific response, the measles antibody and T cell responses were comparable. There were no serious adverse events. Fever was slightly higher in the aerosol group.

There are a number of problems associated with the "classic Mexican" device, not least is that it is not suitable for mass vaccinations in remote parts of the world. The device was difficult to use, bulky, required large batteries or mains powered sources and did not produce consistent results. Dosages were calculated by timing the inhalation period. Hence, the amount of PFU (plaque forming units) could vary from 2800 to 4000 PFU per child (Fernandez-de-Castro J., et al. *Salud Pulica Mex.* (1997), Vol. 39, pages 53-60). Furthermore, components such as the compressor were found not to be suitable for human use. The compressor needed shutting off between doses and was heavy and not easily portable. Moreover, the compressor used high pressures.

Other problems observed with the device included that some measles vaccines lose their potency due to the raised compressor pressures, even with crushed ice. Furthermore, concerns have been raised about reflux of respiratory pathogens into the device and from the patient interface and subsequent transmittal to other patients. The device does not allow the individual components to be easily washed and sterilized.

Alternative methods of administering measles vaccine have been tried using a foot pump attached to a nebuliser (Khanum S., et al., *Lancet*, (Jan. 17, 1987), pages 150-153). Two strains of vaccine were tried, the Edmonston-Zagreb and the Schwarz vaccine. The simple nebuliser used failed to give as food results as the Mexican studies or studies in the Gambia.

Handheld single dose metered devices for administering individual doses are known.

U.S. Pat. No. 5,215,079 discloses a metered dose inhaler for immunising a patient with a vaccine. The inhaler comprises a canister filled with a drug composition or a vaccine and propellant, a metering valve for emitting the vaccine or drug and an interlock that prevents more than one dose being administered. The device is usually only filled with one dose of vaccine or drug and is disposed of after use. This precludes its use in situations where large numbers of vaccinations are required because of difficulties in transporting large numbers of such single dose inhalers to often remote locations.

Such a device uses the lungs or nasal surfaces to absorb the active drug or vaccine.

US 2003/064032A discloses an alternative aerosol device for delivering drugs, such as insulin, comprising using an atomizer. This produces aerosols with an average droplet size of typically 5 μm. This device is aimed at personal insulin inhalation.

U.S. Pat. No. 5,497,944 discloses metered dose inhalers, liquid medicaments in the form of an atomiser for dispersing medicaments, in solution. The device is a handheld, single user device, ideally suited to individual use.

WO 02/074372 discloses aerosol delivery devices for delivering aerosols into a patient. Such devices are stated to include jet aerosolisers and pneumatic and ultrasonic devices. They are exemplified as being suitable for a wide range of different agents, including pharmaceuticals, chemotherapeutics, immune reagents and vaccines. The size of droplets presented in the patent application range from 5-10 microns.

WO2006/006963 (published 19 Jan. 2006) discloses modified aerosol delivery devices for a wide range of uses comprising removable aerosolising elements having movable elements to expel agents from a chamber.

WO 02/43705 discloses aerodynamically light particles for vaccine delivery to the pulmonary system. The particles are stated to have a mean mass diameter of 5-30 micrometers. A wide range of alternative sizes for the particles is referred to in the document.

The generation of therapeutic aerosols depends on the comminution of liquids into small particles. In the case of vaccines such as measles, the antigen is usually contained within small liquid droplets or particles. The energy for this process is usually produced by compressed air passing over the liquid.

There are a wide variety of variables involved in the identification of nebuliser and compressor design and selection for vaccination, rather than drug (such as salbutamol) administration. Previous trials have used a variety of different pressures, nebulisers, compressors, etc. Compressors, for example, have varied from 30-200 psi and the actual pressure applied has not always accurately been stated. Particle size has also been shown to vary and there is a need to optimise the average size produced to ensure that the particles are efficiently delivered to the lungs of a patient.

The Applicants have now identified a number of parameters and modifications to be made to nebulisers in order to optimise nebulisers for use in the administration of vaccines such as measles vaccine, especially with respect to large scale vaccination programs. This is important as previously it has been necessary to trial nebulisers to see whether they have any potential for use in vaccine development. By identifying the parameters for suitable nebulisers which can be tested within the laboratory, this considerably reduces the numbers of nebulisers which need to be tested for their ability to be used with vaccines.

Other devices for administration of measles and other vaccines have been considered by the Applicants. These include nasal sprays. However, a problem associated with nasal sprays is that upper respiratory tract infections often interfere with it. The devices produce mean particle sizes of about 70 microns. These large particles often do not pass past the vocal cords. As measles vaccine is thought to be ideally absorbed by the lower respiratory tract, the size of the particles produced by nasal sprays are thought to be a major problem.

Dry powder delivery has also been considered. However, initial results by the Applicants indicated that the dry powder is often deposited in the large bronchi and not properly taken into the lower respiratory tract. Furthermore, there may be difficulties with infants because of the relatively large doses required to administer the required amount of vaccine.

U.S. Pat. No. 6,630,169 discloses compositions and methods for the administration of particulates. Such particulates may be in the form of dry powders or combined with non-aqueous media to form stabilised dispersions. The compositions may be used in conjunction with metered dose inhalers, dry powder inhalers, atomisers or nebulisers, but also suggests topical, intramuscular, transdermal, intradermal, intraperitoneal, vaginal, rectal and occular administration routes for the particulates. Vaccines, microbes, vectors, polypeptides, proteins, carbohydrates and peptides are among the many different biologically active materials suggested in the patent. The patent is concerned with the production of specific dry powder formulations which have reduced clumping of the particles. The document speculatively suggests a wide range of particle sizes for the dry particles of between 0.5 μm and 50 μm, with preferred mean geometric dry particle sizes of less than 20 μm or even less than 1 μm. The spread sizes of particles are not provided in the document.

DESCRIPTION

The applicants have identified a number of parameters to allow nebulisers, including commercially available nebulisers previously used for drug delivery, to be adopted to be used with a variety of vaccines. This is especially useful because some different vaccines work best by being absorbed by different parts of the lung. Measles vaccine, for example, works best by absorption through the lower respiratory tract, rubella vaccine works better further up the respiratory tract. This opens the nebulisers to being used for two or more different vaccines.

The factors identified by the applicants for creating a nebuliser device suitable for use in the field include:
1. Optimal particle size for a variety of different vaccines;
2. Increased vaccine potency retention without the need for cooling;
3. Reduced contamination between patients by using disposable elements, filters and one way valves;
4. Consistent dose delivery;
5. Portability and alternative energy sources;
6. Needle-free loading of vaccines to reduce the risk of contaminated sharps.

The invention provides a method of selecting or optimising a nebuliser device to be used to deliver a vaccine comprising selecting a nebuliser capable of producing a plurality of vaccine particles having the following particle droplet size distribution:
  (i) $D_{v10}$: 2.0+/−0.2 μm
  (ii) $D_{v50}$: 5.0+/−0.5 μm
  (iii) $D_{v90}$: 10.0+/−1.0 μm.

The mean mass aerodynamic diameter (MMAD) is 4.5 to 8.0 μm, especially approximately 6.5 μm, with a Geometric Standard Deviation (GSD) of 1.7. This has been found to be especially useful measurement for determining the optimum size distribution for the particles The inventors have realised that having a nebuliser device capable of producing particles of different sizes allows the nebuliser to be used with different vaccines. Hence, as indicated above, the device may be used with measles vaccine which optimally uses particles which are small enough to be transported to the small alveoli of the lungs, and also be used with vaccines such as rubella which optimally require larger particles which are deposited further up the respiratory tract. The ability to use one nebuliser device with a variety of different vaccines is very useful. This means that it can be easily used in the field without having to optimise the individual nebuliser for individual vaccines. Furthermore, having the variety of particle sizes allows combinations of different vaccines with different requirements, such as the combination of measles and rubella vaccine to be used.

Other preferred vaccines include: measles, rubella and mumps, influenza, HPV, SARS, hepatitis, yellow fever, BCG, Meningococcal C, HIV and dengue.

The term "vaccine" preferably means a preparation of antigenic material that can be used to stimulate the development of antibodies and thus confer active immunity against a specific disease or a number of diseases.

The sizes of particles may be determined via techniques known in the art. For example, particle sizes using optical devices, such as lasers, to determine particle sizes are known. An example of such a laser particle sizer is the "Malvern Mastersizer X: Model MSX", produced by Malvern Instruments Limited, Malvern, Worcestershire, United Kingdom. This is a standard instrument which is accepted by regulatory agencies world-wide as a standard method of determining particle sizes.

The vaccine particles may be dry vaccine particles. They may also be aerosols of liquids containing active vaccine.

Preferably, the amount of vaccine having a diameter of less than 10 μm diameter is greater than 85, greater than 90, greater than 95 or 100%.

Preferably, the number of vaccine particles having a mass diameter of less than 5 μm is between 50 and 60%. The number of vaccine particles having a diameter of less than 3 μm diameter is preferably 25-30%, especially 30%.

The mean mass aerodynamic diameter (MMAD) is 4.5 to 8.0 μm, especially approximately 6.5 μm, with a Geometric Standard Deviation (GSD) of 1.7. This has been found to be especially useful measurement for determining the optimum size distribution for the particles.

Vaccine particles of less than 0.5 μm in diameter may be re-expelled from the lungs. Hence, preferably at least 90%, more preferably 95%, 98%, especially 100% of the particles produced by the nebuliser selected by the method of the invention are greater than 0.5 μm in diameter.

Aerosol particles that can transverse the pharynx and upper airways are generally less than 6 μm MMAD. Particles of less than 2 μm MMAD can transverse artificial airways such as endotracheal tubes and can also reach the smaller airways of the lungs.

Particles of less than 0.6-0.3 μm MMAD are often exhaled, although particles of <0.1 μm MMAD can diffuse out of the ventilatory air stream and settle on airway surfaces.

The size distribution is optimised to allow the devices identified by the method to be used with a variety of different vaccines, such as monovalent and combined vaccines, and to be used with a variety of different patients of different ages and different breathing sizes and rates.

As indicated above, some vaccines work best by deposition on, for example, mucous glands and smooth muscle and hence should be deposited in the proximal airways, such as the first 6 generations of the tracheobrochial tree. Others work better by deposition deeper into the lungs.

The conditions for selecting the nebulisers allows the selection of nebulisers suitable to be used with a wide variety of different patients and vaccines. Previously this would have required the individual testing of each device with different vaccines and with different patients. The method of the invention screens out less suitable devices without the need for clinical testing. This reduces cost and speeds up the time taken to identify and utilise suitable devices.

The identification of the parameters for selecting a nebuliser is important. There are a large number of different commercially available nebulisers on the market that are currently used for delivery of drugs, such as Salbutamol. The ability to select such nebulisers for use in conjunction with the vaccine by one or more easily testable parameters without having to go to clinical trials, considerably eases the process of identifying suitable nebulisers for vaccine production. For example, the applicant reviewed 18 different commercially available nebulisers. Not all of the nebulisers produced the particle sizes with such a size distribution. Hence, it was possible to select some of those nebulisers which did have a suitable size distribution, prior to having to undertake clinical trials.

Preferably, the nebuliser device is provided with a receptacle for receiving two or more doses of vaccine. That is, the nebuliser device is not a single dose nebuliser, but is capable of being used in a mass vaccination program. Typically, the receptacle will hold 5, 10, 15, especially 20 or more doses of vaccine, most preferably 40 or less doses of vaccine. The ability to have a number of different doses of vaccines considerably increases the speed of which the device may be used.

Ideally, the device should be able to be used with a delay of preferably less than 1 minute, or as little as 30 seconds, between individuals. Use of the vaccine in the field means that ideally the nebuliser should be selected to produce a substantially constant dose delivery between uses. For example, the compressor or other gas delivery means may be a part of the nebuliser device, and which may be used to either generate the vaccine aerosol and/or propel the vaccine aerosol into the lungs of a user, should be selected so that there is substantially no variation between individual doses delivered to a patient when in use. For ease of use, the dose should preferably be preset.

Preferably, the amount of vaccine delivered by the device is selected to be less than 1 ml, especially 0.1, 0.2, 0.3, 0.4, 0.5, 0.6, 0.7, 0.8 or 0.9 ml. Most preferably the dose is 0.25 ml. The rate at which the vaccine is delivered may be adjusted, for example, by varying the flow rate of the air intake from the compressor or other gas delivery means.

Preferably the rate at which vaccine is delivered is between 0.2 and 0.4 ml/min., more preferably between 0.34 and 0.40 ml/min.

Preferably an immunizing dose of vaccine is delivered in a time of between 20 and 40 seconds, preferably about 30 seconds to ensure that sufficient vaccine is delivered to a child or infant by the child or infant breathing in or inhaling the vaccine. An immunizing dose is preferably one which provides enough vaccine to provide immunity to the child or infant. This amount of time is optimized to ensure that the vaccine is delivered quickly, whilst ensuring that sufficient time is provided to allow the infant or child to inhale the vaccine.

The nebuliser may be breath activated. That is, the patient breaths in, causing a reduction in pressure in, for example, a mouthpiece, which activates the nebuliser. Such devices are known, but allow the nebulisers to be used more easily.

Where a compressor is used, the compressor preferably comprises a filter capable of filtering airborne microorganisms. This reduces the risk of cross-contamination with pathogens from the patient or surroundings because of the pathogens being uptaken by the compressor and then subsequently being expelled into other patients.

One problem identified with prior art nebulisers has been the requirement to have cooling of the vaccine once it has been reconstituted prior to use. Particularly, such cooling has required the use of ice or other complicated cooling means. In remote or isolated regions, such as in the tropics, the availability of ice is often limited. Furthermore, such cooling systems add to the complexity and bulk of the device. Hence, preferably the method of selecting or optimising a nebular device comprises selecting a nebuliser which in use has at least 75% potency retention for reconstituted vaccine delivered by the nebuliser to a patient. Preferably the vaccine potency is at least 75% of the starting potency of Edmonston-Zagreb vaccine after 40 doses. That is, between the first dose delivered to a first patient, and the last dose of a batch of vaccine in the nebuliser given to the last patient, there is only approximately 25% loss of potency. Methods of detecting vaccine potency retention are themselves known in the art.

The potency retention method permits the assessment of different vaccine strains aerosolized by various nebulizers, and the subsequent selection of the most appropriate strain/nebulizer combination.

For Example, three methods have been developed by the Health Protection Agency (HPA) of the UK MHRA. For each method, virus emitted from the nebulizer in aerosol form is captured into cell culture media, and the virus concentration in this cell fluid is then measured by infecting Vero cells and determining the infectious units by a method called Plaque Reduction Neutralization (PRN) which is routinely used for measuring measles titres. The potency before and after nebulization is determined and the reduction calculated.

In two later methods, a tracer molecule (e.g. sodium fluoride or others) is added at a known concentration to the virus before nebulizing. The amount of tracer in the captured virus is measured and a correction factor for the loss of tracer is applied to the virus concentration to give the final potency retention value.

All methods are performed in a biosafety cabinet.

Method 1: Samples are collected from the aerosol by allowing it to condense on a cold surface for a specific amount of time, and the condensate put into cell culture medium and then sampled and tested for virus concentration.

Method 2: All-Glass Liquid Impinger (AGI 30)

Aerosolized vaccine is delivered over a specific amount of time directly into the aperture of a glass chamber containing a known amount of cell culture fluid. A pump ensures that the aerosol is drawn through into the fluid.

Method 3: MBI Sampler.

This sampler is routinely used for sampling air in "clean" areas. For air sampling a Petri plate of agar captures any microorganisms that enter via the vacuum pump drawing in a specific volume of air.

For the aerosol, the agar plate is replaced with a cell culture dish. The virus captured in the cell fluid is measured by PRN. This use of the MBI has been developed for this measles aerosol project.

The applicants believe that one of the major problems associated with the "classic Mexican device" which reduces vaccine potency is the high turbulence generated by the nebulisers used in that device. This appears to disrupt the vaccine particles or components, resulting in reduced potency, and hence the need to have ice to stabilise the vaccine. The applicants have found that selecting the nebuliser element, that is the part of the nebuliser that creates the aerosol particles, can be used to increase vaccine potency. In particular, one preferred example they have identified, is the use of a piezoelectric nebulising means.

Nebuliser means or elements are themselves known in the art per se. They are sometimes also known as nebuliser "micropumps".

Preferably, the nebuliser is a piezoelectric nebuliser. Nebulisers have been produced for the inhalation of drugs utilising piezoelectric vibrated mesh or plates, vibrating at high frequency. Examples of piezoelectric nebulisers (also known as vibrating element nebulisers) are known in the art for drug usage, but not vaccine use. For example, a number of types are manufactured under the trade name "Aeroneb" by Nektar Inc, or "e-flow" by Pari.

Such devices often use a ceramic vibrational element and domed aperture plate. Contraction and expansion of the vibrational element produces an upward and a downward movement of the domed aperture plate. the plate may contain up to 1000 tapered holes. Medication placed in a reservoir above the apertured plate is pumped through the holes in the plate to produce the aerosol. Ultrasonic piezoelectric nebulisers are also shown in, for example, EP 0516565A.

An advantage of this system is that aerosol particle size and flow rate can be modified for the parameters identified by the Applicants. Furthermore, initial results indicate that vaccine potency retention can be considerably higher than that obtained with the "classic Mexican device" whilst still ensuring good delivery of the dose. This may be due to less turbulence and energy being imparted on the device compared to the strong jet of air used with the prior art devices. The device can also be used without the need for crushed ice (used with the Mexican device). The devices use considerably lower power consumption, thus leading to use of smaller, rechargeable, power supplies.

The advantage of a piezoelectric nebuliser is that the particle size is fairly accurately controlled. Furthermore, the piezoelectric nebuliser uses lower amounts of energy, thus allowing smaller and lighter batteries to be used. Such batteries may be rechargeable, such as nickel metal hydride batteries.

Jet nebuliser devices may also be used. Such devices include, for example handheld devices such as the CompAir Elite™ Compressor Nebulizer (NE-C21V) from Omron Healthcare Inc.

The vaccine is preferably chilled to 2-8° C. once reconstituted prior to adding to the nebuliser device or between batches of vaccinations.

Preferably, in addition to concerns about the retention of potency during nebulization, the vaccine is to be reconstituted with cold diluent (according to the manufacturer) and once loaded into the nebulizer, the latter is preferably able to be detached and stored according to international cold chain requirements without the risk of contamination in order to maintain potency during any time there is a break in administration during the vaccination session. Hence, preferably, the receptacle for receiving the two or more doses of vaccine, optionally together with the nebulising means is detachable to allow the receptacle, with vaccine in place to be stored between vaccinations, substantially without contaminating the vaccine within the receptacle.

The Applicants also identified that the ability to use a close-fitting mask reduces the amount of contamination of the surroundings via extraneous vaccines. Hence, preferably the nebuliser is selected to have a face mask, or other suitable interface such as a mouthpiece, which is adapted to fit substantially to the contours of the patient's face when in use.

The nebuliser may additionally comprise a spacer between the nebuliser and, for example, the face mask, mouthpiece, or nasal prongs. A spacer is a chamber. Instead of inhaling directly from the nebuliser and the face mask, a dose from the nebuliser is sprayed into the spacer and then air within the spacer is inhaled through a mouthpiece, or mask. The advantage of the spacer is that it is not necessary to coordinate with the nebuliser. It is possible to breath in and out several times with the chamber and reduces the amount of vaccine that is deposited within the mouth and throat, rather than entering the lungs. This also reduces the amount of vaccine that is swallowed and absorbed from the intestine into the rest of the body. This can therefore improve the amount of vaccine uptaken, or reduce the amount of vaccine needed to produce a sufficiently high dosage for the patient.

Alternatively, the face mask itself may be adapted to produce a sufficiently large volume to mimic the effects of having a separate spacer.

One or more hoses may be provided between the individual components, for example between the compressor and nebuliser or the nebuliser and the face mask, mouthpiece or nasal prongs. The hose may be flexible. This improves the ease of which the nebuliser can be used.

Suitable patient interfaces include the following:

| Twelve months old | Six years old |
|---|---|
| CompAir Elite (Omron), with valved mask. | CompAir Elite (Omron), with collapsible VHC. |

-continued

| Twelve months old | Six years old |
|---|---|
| Aeroeclipse (Trudell), with valved mask. | Aeroeclipse (Trudell), with valved mouthpiece. |
| Aeroneb Go (Aerogen), with valved mask. | Aeroneb Go (Aerogen), with collapsible VHC-Thayer. |

Preferably, the method involves selecting a nebuliser in which one or more of the receptacle, nebuliser element, face mask, mouthpiece, nasal prong, filter or air hose are disposable. In remote areas it is often very difficult to provide cleaning materials, such as clean water, to clean the components of the nebuliser. Hence, having, for example, a disposable nebuliser element, can considerably reduce the risk of cross-contamination between patients or between users. The face mask or other patient interface, for example, may be made of disposable paper and may be disposed of between patients.

Further reduction in contamination may be obtained by utilising a one-way valve between the patient, a nebuliser element and/or a compressor when used to prevent pathogens from the breath of a patient entering, for example, the nebuliser element, receptacle or compressor.

The materials that the nebuliser device is made of is preferably biocompatible and is preferably compatible with the high humidity and/or temperatures found in tropical or desert regions.

The method of invention preferably includes the step of selecting the weight of the nebuliser. It is important that the nebulisers be usable within the field. Hence, preferably the nebuliser weighs less than 3 kg, especially less than 2.5 kg, more preferably less than 2 or less than 1 kg.

Preferably, the compressor and nebuliser are sufficiently small to allow the compressor and nebuliser to be handheld.

Preferably, the energy source for the nebuliser is selected so that it can be used in the field. For example, the nebuliser preferably comprises a rechargeable battery, such as a nickel cadmium battery. Such batteries may be readily recharged, for example, via the use of local mains electricity, or generator electricity where available. Alternatively, they may be recharged in the field utilising a solar panel. Alternatively, the nebuliser may be powered manually, for example, via the use of a foot pump. One drawback with foot pumps has previously been the ability to create consistent flow rates and particle sizes. Hence, the method of selecting the nebuliser allows the screening of unsuitable nebuliser devices. Two or more different methods of powering the device, such as battery or mains, or different voltages such as 12V or 240V may be used to power the device. This allows the device to be easily used in a variety of field situations.

Preferably, the nebuliser device is provided with a needle-free vaccine loading device. A major problem in the field is the disposal of, for example, syringe needles.

The vaccine is preferably added without the use of a syringe. One way of doing this is to provide individual doses, or predetermined amounts, in a sealed container (such as a vial) with a frangible seal that can be broken to allow access to the vaccine. The container may comprise two compartments separated by a frangible barrier, one containing e.g. a predetermined amount of water, the other containing lyophilized vaccine. Breaking the barrier allows the water and vaccine to be mixed, prior to being added to the receptacle. Such needle-free delivery systems reduce the possibility of having contaminated sharps to be disposed of. Alternatively, syringes without needles on their ends may be used.

The invention also provides, in combination, a nebuliser having two or more of the characteristics identified by the claimed invention in combination with a vaccine.

A further aspect of the invention provides a nebuliser device comprising two or more of the following properties:
(a) in use, the nebuliser device is capable of producing vaccine particle mass diameters of:
 (i) at least 80% less than 10 μm;
 (ii) 45 to 65% less than 5 μm; and
 (iii) 20 to 40% less than 3 μm.
(b) a piezoelectric nebulising element;
(c) an air delivery element, such as a compressor, having an air intake filter capable of filtering airborne microorganisms;
(d) a face mask, or other suitable facial interface, adapted to fit substantially to the contours of the face of a patient;
(e) a nebuliser element attached to a face mask adapted to fit substantially to the contours of a patient's face when in use;
(f) a one-way valve between the patient, a nebuliser element and/or a compressor;
(g) a rechargeable receptacle, for example after one load/vial of vaccine is introduced;
(h) one or more of a receptacle for receiving a supply of vaccine, a nebuliser element, a mouthpiece, a nasal prong, a filter and/or an air hose are disposable.

Preferably, the nebulisers are used in combination with a vaccine.

The nebuliser device preferably comprises 3, 4, 5, 6, 7 or all of the features identified above. The individual components are preferably as described above for the first aspect of the invention.

Preferably, the nebuliser is used in combination with 1, 2 or more vaccines.

Typically, the dosage provided is at least 1000 PFU (plaque forming units) of the vaccine (typically 1500 PFU). Preferably, the vaccine concentration per liter of air produced by the nebuliser is 300-500 pfu/liter, especially 300-400 pfu/liter.

The vaccine may be any suitable vaccine. However, preferably the vaccine is a measles vaccine. Especially preferred strains of measles vaccines include the Edmonston-Zagreb measles vaccine produced by The Serum Institute of India.

The preservation of vaccines such as measles vaccine by, for example, desiccation, freeze-drying, chilling and other techniques, is known in the art. For example, WO 00/78924 discloses preserving viruses, proteins and nucleic acids using trehalose and coacerevate combined with desiccation. The material may be rehydrated prior to use. Similarly, WO 00/66710 discloses utilising desiccation and trehalose to preserve viruses for use in vaccines.

It is also known to adapt vaccines so that they are uptaken via intranazal or inhalation better. EP 0440289 discloses utilising liposomes. U.S. Pat. No. 6,017,513 discloses mixtures of polymers, such as oligosaccharides or polysaccharides, optionally together with an amphiphilic compound or lipid, to improve the uptake of antigens on nasal administration.

WO 00/00215 discloses utilising particulates comprising, for example, phospholipids with antigenic material such as viruses. These may be used with metered dose inhalers, dry powder inhalers, atomizers and nebulisers.

The invention also provides a method of administering a vaccine comprising providing a vaccine as an aerosol via a nebuliser as defined in any previous aspect of the invention.

Vaccine kits comprising a nebuliser according to the invention in combination with a vaccine, preferably comprising a rechargeable batter as a source of energy for the nebuliser device, are also provided.

The kit is preferably provided in a watertight, lockable carrying case for use in the field.

The applicants have developed recommended screening and final test criteria to identify suitable nebulisers:
Preferred Recommended Performance Data for Comparison with Candidate Device
Screening Criteria:
1. Average output should be comparable or greater than results shown below:
IPI Nebulizer Output:
 0.34-0.40 ml/min
2. Droplet size distribution: Average $D_{v10}$, $D_{v50}$ and $D_{v90}$ should be comparable to results shown below:
IPI Nebulizer Particle Size (Using Malvern Mastersizer X):
 Average $D_{v10}$: 2.0±0.2 μm
 Average $D_{v50}$: 5.0±0.5 μm
 Average $D_{v90}$: 10.0±1.0 μM
Final Test Criteria:
Devices that demonstrate acceptable output and particle size distribution and satisfy all other criteria (i.e. portability, clean ability, low or zero potential for cross-contamination, etc.) should be retested with Edmonston-Zagreb vaccine for output, particle size and virus viability by an independent laboratory.

During this final testing, particle size must be determined using an impactor.
Vaccine should be tested while cold (preferably 2-8° C.
To test for vaccine viability with standard jet nebulizers, 0.5 ml samples should be removed from the aerosol generator reservoir for assay at time 0, and after 5, 10, 20 and 40 doses of 30 seconds each.
To test for vaccine viability with devices that deliver aerosol via vibrating-mesh technologies, virus potency in the emitted aerosol should also be tested.

Output, particle size and potency should be comparable to:
1. IPI Nebulizer Output:
 0.34-0.40 ml/min (based on results reported by Drs. Allan Coates and John Bennett for classic Mexican device for live-attenuated virus).
2. IPI Nebulizer Particle Size for plaque forming units (Using Malvern Mastersizer).
 MMAD: 6.5 μm
 GSD: 1.7
3. Vaccine Potency should be at least 75% of the starting potency of Edmonston-Zagreb vaccine after 40 doses.

The invention will now be described by way of example only with reference to FIG. 1.

A number of different devices, including jet nebulisers and vibrating element nebulisers, were evaluated. Three devices that currently need licenses for drugs, but not vaccines, were identified. These devices are known in the art. They had not previously been selected to be used for vaccines.

Studies on Particle Sizing of the Measles Vaccine Using the Malvern Mastersizer X.

The applicants identified that the "classic Mexican device" had a number of advantages in vaccine uptake. They therefore identified the advantageous parameters associated with the device for application to other devices.

The following shows the typical methods used to test the devices. Further experimentation and deliberation of the results on behalf of the applicants produced the size recommendations claimed for the invention.

Materials:
Equipment
Evans Compressor: model T045ME075-P, serial number 22-117-1233.

Osmometer: model 3300, Advanced Instruments, serial number 9905 0526
Balance: Sartorius, model BL 150
Pressure/flow meter: Timeter, series RT-200, Timeter Instrument Corp, Serial number Q17C
Malvern Mastersizer X: model MSX, Malvern Instruments, serial number 333371/18 Malvern computer programme version 2.19, Malvern Instruments Ltd. (instrument based on the Mie theory of particle sizing (transparent droplets))
Digital Timer Marathon
Vaccine
Measles virus vaccine, live, attenuated, lyophilized, 10 dose vials
  Manufactured by the Serum Institute of India, Ltd
  a) Lot # EU1974, expiry September 2003
  Diluent used: WFI, Baxter, lot # W2D18A0, expiry April 2003
  b) Lot # EU2593, expiry July 2005
  Diluent supplied: WFI, SILL lot 1749, expiry October 2008
Supplies
Disposable pipette tips for osmometer: 20 μl
Syringes and needles for reconstitution and withdrawal of vaccine
Nebulizer with mouthpiece, oxygen tubing (2 m), and T piece.
  IPI Model C4101, Lot L010.
Corrugated plastic tube (spacer), 15 cm
Ring Clamps
Procedures:
Malvern Mastersizer X Calibration:
  The equipment was calibrated using 9 um latex particles by Lisa Painchaud (Malvern Instruments Inc.) on May 27, 2003. Performance Verification Certificate #MSUPOQ13 and the test results were issued and are on file at the laboratory.
Laser Alignment and Background Determination.
  This is automatically run by the computer programme.
Compressor Setting.
  After the initial setup experiments, the Timeter, a flow and/or pressure measuring device (range 0-100 psi), was used to determine the actual pressure of air driving the nebuliser for the 40 psi setting on the Evans Compressor. The compressor pressure adjustment was fixed at 40 psi on the dial which was the setting used during the Mexican studies. The flow was determined by connecting the corrugated spacer tube of the assembled device to the input of the Timeter, turning on the compressor, and waiting for the flow reading on the Timeter to stabilize. Flow readings were taken and recorded for each day that nebuliser run(s) were performed. Pressure was also measured by incorporating a "y" in the $O_2$ tubing connecting the nebuliser and compressor. The third port was connected to the Timeter, and the pressure reading was taken once stabilization occurred.
Nebulisation of Vaccine.
  The MastersizerX is turned on and is aligned and the background determined by the computer programme. (The room is darkened to avoid extraneous light). A 100 mm lens size is used for accurate measurement of particles of <20 μm. The MastersizerX is set for 2000 sweeps after pressing the space bar on the computer (2000 readings of the aerosol stream before stopping and calculating the particle sizes and distribution and printing out on the computer screen).
  The four nebulisers are permanently labeled as A, B, C, and D. The T piece is blocked at one end of the T.
  Before each run, the nebuliser apparatus (nebuliser cup and lid, mouthpiece, T piece, and corrugated spacer tube) are weighed and the weight recorded.

The measles vaccine is reconstituted with 5 mL WFI diluent by syringe, swirled to completely dissolve, extracted, and 3 mL is placed in the nebuliser cup. (Note, for several runs on one day, 2 vials are reconstituted, mixed, and used for up to 3 runs. Reconstituted vaccine is kept on crushed ice).
  A 20 μl sample is removed for determining the osmolarity.
  The nebuliser apparatus is assembled with the mouthpiece at the outlet of the corrugated spacer tube (to focus the aerosol outflow) and re-weighed with vaccine. The weight is recorded. The nebuliser with vaccine is placed in a container of crushed ice as recommended during aerosolization.
  The oxygen tubing from the compressor is fitted and clamped to the nebuliser inlet.
  The nebuliser apparatus is clamped to a stand with the mouthpiece outlet at perpendicular to and approximately 2 cm away from the laser beam.
  The digital timer and the compressor (setting fixed at 40 on the regulator) are turned on simultaneously.
  During the first two minutes of aerosol output, the apparatus is adjusted to be in the correct position and perpendicular to the laser beam, and to be in the acceptable range of laser obscuration (green zone on the computer screen) indicating that the aerosol stream is passing directly through the laser beam.
  At approximately 2 minutes after the run is started, the space bar on the computer is pressed to start the first measurement. The run continues for up to 5 minutes at which time the compressor is turned off. During a run a second or third measurement can be taken at 3 or 4 minutes by again pressing the space bar. The start time of each measurement and the total run time is recorded by the operator. (If the aerosol fogs the lens, the lens may need cleaning before another measurement is taken).
  After the run is complete, the nebuliser with the remaining vaccine is disconnected and the nebuliser components are wiped down, re-weighed and the weight recorded. A 20 of sample is then taken for osmolarity check.
  The vaccine is discarded, the nebuliser cleaned and dried for the next run.
  Note: In several runs, a supplemental flow was added via a concentric tube around the output corrugated spacer tubing. The concentric tube is 9 cm long, and its outlet was placed flush with the end of the corrugated spacer tubing outlet. Supplemental flow was added from the air source via a "y" connector—with one arm connected to the concentric tube around the corrugated spacer tube and one arm open to the atmosphere. This setup allowed the additional air to mix with the nebuliser output only at the end of the corrugated spacer tube. This setup was designed to increase flow without disturbing the particle output for a different experiment (not relevant here). The third port of the "y", open to atmosphere, prevented any possible build up of pressure in the system. The supplemental flow was set to >20 lpm. Supplemental flow is not used for the concentration calculation as it does not alter the characteristics of the aerosol (flow is 100% RH and exact temperature of output of nebuliser), gravimetric changes in the nebuliser, or osmolarity.
Results
  A total of 18 runs of particle sizing of aerosolized measles vaccine were performed using 4 different nebulisers from the same production lot. In May 2003, the runs were done with no supplemental air added. In November 2003 and February 2004, supplemental air flow of 20 L/min was added at the mouthpiece. This would mimic a large child breathing in with flows greater than the output airflow.

Trial Runs to Establish Settings using Three Nebulisers.
Vaccine lot number EU1974.

|  | Nebuliser A | Nebuliser B | Nebuliser C |
|---|---|---|---|
| Date | May 27, 2003 | May 28, 2003 | May 28, 2003 |
| Compressor flow (L/min) | 9.4 | 9.4 | 9.4 |
| Compressor pressure (psi) | 41.1 | 41.4 | 41.4 |
| Weight of nebuliser before (gm) | 96.96* | 43.86 | 43.88 |
| Weight plus vaccine before (gm) | 99.99* | 46.93 | 47.11 |
| Weight after nebulisation (gm) | 98.14* | 45.29 | 45.8 |
| Osmolarity before (mOsm) | 78 | 79 | 79 |
| Osmolarity after nebulisation (mOsm) | 94 | 94 | 93 |
| Total run time (min) | 4 | 4 | 4 |
| Time of sampling (min) | 2 | 2 | 2 |
| Laser obscuration (%) | 23.3 | 27.3 | 23.0 |
| MMD (μm) | 4.74 | 4.47 | 4.71 |
| % < 3 μm | 27.78 | 35.13 | 28.9 |
| % < 5 μm | 51.95 | 62.2 | 54.4 |
| % < 10 μm | 86.81 | 93.24 | 87.12 |

*tubing also weighed with the nebuliser components for this run.

Note:
after these runs it was decided to fix the compressor at the 40 psi setting as used in Mexico, and measure the actual pressure used, rather than try to set the compressor to deliver 40 psi as was done here. This was to ensure that the study determined the particle sizes as used in the clinical studies.

Study Runs with Three Nebulisers:
Vaccine lot number EU1974.

|  | Nebuliser A | | Nebuliser B | Nebuliser C | |
|---|---|---|---|---|---|
| Date | May 29, 2003 | | May 29, 2003 | May 29, 2003 | |
| Compressor flow (L/min) | 10.2 | | 10.7 | 10.0 | |
| Compressor pressure (psi) | 46.2 | | 46.9 | 46.9 | |
| Weight of nebuliser before (gm) | 53.91 | | 54.15 | 54.24 | |
| Weight plus vaccine before (gm) | 56.97 | | 57.15 | 57.54 | |
| Weight after nebulisation (gm) | 55.71 | | 55.61 | 56.05 | |
| Osmolarity before (mOsm) | 79 | | 79 | 79 | |
| Osmolarity after nebulisation (mOsm) | 90 | | 94 | 96 | |
| Total run time (min) | 2.43 | | 3.5 | 3.5 | |
| Time of sampling (min) | 2 | | 2 | 2 | |
|  | 2.4 | | | 3 | |
| Laser obscuration (%) | 16.0 | 16.0 | 15.5 | 22.9 | 13.5 |
| MMD (μm) | 4.47 | 4.49 | 4.02 | 4.36 | 4.45 |
| % < 3 μm | 35.74 | 31.0 | 37.8 | 32.28 | 31.60 |
| % < 5 μm | 60.77 | 57.41 | 63.94 | 57.49 | 56.26 |
| % < 10 μm | 91.33 | 89.19 | 93.86 | 90.02 | 89.06 |

Runs with Supplemental Air Supplied at the Mouthpiece Using 4 Nebulisers.

A: Vaccine Lot Number EU1974. (Lot Expired September 03, but Particle Size should not be Affected)

|  | Nebuliser A + Supplemental air flow | | | Nebuliser B + Supplemental air flow | | |
|---|---|---|---|---|---|---|
| Date | Nov. 25, 2003 | | | Nov. 26, 2003 | | |
| Compressor flow (L/min) | 10.2 | | | 10.7 | | |
| Compressor pressure (psi) | 46.2 | | | 46.9 | | |
| Weight of nebuliser before (gm) | 62.23 | | | 62.40 | | |
|  | 61.80 | | | 61.89 | | |
|  | 61.7 | | | 63.31 | | |
| Weight plus vaccine before (gm) | 67.04 | 66.75 | 66.56 | 67.16 | 66.48 | 68.21 |
| Weight after nebulisation (gm) | 65.02 | 64.86 | 64.69 | 65.53 | 64.71 | 66.44 |
| Osmolarity before (mOsm) | 79 | 77 | 75 | 81 | 81 | 77 |
| Osmolarity after nebulisation (mOsm) | 88 | 86 | 83 | 87 | 87 | 85 |
| Total time of run (min) | 5 | 5 | 5 | 5 | 5 | 5 |
| Time of sampling (min) | 1.5 | 1.5 | 2.5 | 1.5 | 2 | 2 |
| Laser obscuration (%) | 20.7 | 16.2 | 17.3 | 16.5 | 14.9 | 14.0 |
| MMD (μm) | 5.01 | 4.82 | 4.92 | 5.08 | 4.95 | 4.79 |
| % <3 μm | 24.56 | 26.51 | 25.12 | 21.84 | 25.29 | 25.55 |
| % <5 μm | 49.88 | 52.13 | 50.92 | 48.91 | 50.55 | 52.63 |
| % <10 μm | 87.27 | 88.22 | 88.14 | 90.09 | 87.53 | 89.86 |

Note -
the nebulisers were run three independent times, with cleaning and drying of the apparatus between, only one reading of the compressor flow and psi was taken at the beginning of each day)

B: Vaccine Lot Number: EU2593, Expiry July 05

|  | Nebuliser C + Supplemental air flow | | | Nebuliser D + Supplemental air flow | | |
|---|---|---|---|---|---|---|
| Date | Feb. 12, 2003 | | | Feb. 17, 2003 | | |
| Compressor flow (L/min) | 10.0 | | | 10.7 | | |
| Compressor pressure (psi) | 46.9 | | | 46.9 | | |
| Weight of nebuliser before (gm) | 62.95 | | | 62.88 | | |
|  | 63.02 | | | 62.96 | | |
|  | 63.09 | | | 63.31 | | |
| Weight plus vaccine before (gm) | 66.09 | 66.34 | 66.99 | 66.03 | 66.11 | 67.16 |
| Weight after nebulisation (gm) | 64.48 | 64.69 | 65.37 | 64.35 | 64.34 | 65.17 |
| Osmolarity before (mOsm) | 89 | 85 | 84 | 86 | 86 | 86 |
| Osmolarity after nebulisation (mOsm) | 100 | 97 | 94 | 98 | 104 | 101 |
| Total time of run (min) | 5 | 5 | 5 | 5 | 5 | 5 |
| Time of sampling (min) | 2 | 2 | 3 | 3 | 3 | 3 |
| Laser obscuration (%) | 19.0 | 23.6 | 15.5 | 15.3 | 14.3 | 14.8 |
| MMD (μm) | 4.45 | 4.63 | 4.61 | 5.21 | 5.18 | 5.18 |
| % <3 μm | 30.41 | 29.55 | 28.76 | 24.02 | 24.53 | 24.31 |
| % <5 μm | 56.47 | 54.11 | 54.44 | 47.62 | 48.01 | 47.96 |
| % <10 μm | 89.73 | 87.82 | 88.69 | 86.04 | 85.94 | 85.94 |

(Note - the nebulisers were run three independent times, with cleaning and drying of the apparatus between, only one reading of the compressor flow and psi was taken at the beginning of each day)

Calculations:

The theoretical output of vaccine from the nebuliser can be calculated by the following formulae. The effect of the nebulisation process on the stability of vaccine potency has not been taken into account.

Vaccine nebulised: calculated from the weight lost during the run.

Volume nebulised (gm)=nebuliser plus vaccine pre (gm)−nebuliser plus vaccine post (gm)    I:

Rate of output of the aerosolized vaccine from the nebuliser in mL/minute: calculated from the loss of volume in gms (=mL) from the nebulisers/connectors divided by the time of the run:

Vaccine output (mL/min)=Volume nebulised (mL)/time of run (min).    II:

Vaccine nebulised in pfu/minute.

Pfu/min=Potency of vaccine (pfu/mL)×Vaccine output (mL/min)    III:

Vaccine concentration in the aerosol is the concentration of virus particles in the air flowing out of the nebuliser.

Vaccine conc'n (pfu/L)=vaccine nebulised (pfu/min)/compressor air flow (L/min)    IV:

Calculations for Each Run:
Assuming the vaccine potency is $10^4$ pfu per mL:

| MMD Range | % ≤ 3 μm diam | % ≤ μm diam | % ≤ μm diam |
|---|---|---|---|
| Nebulizer A: 4.47 to 5.01 μm (av 4.74) | 24.56 to 35.74 | 51.95 to 60.77 | 86.82 to 91.33 |
| Nebulizer B: 4.02 to 5.08 μm (av 4.66) | 21.84 to 35.13 | 48.91 to 63.94 | 87.53 to 93.86 |
| Nebulizer C: 4.36 to 4.71 μm (av 4.54) | 28.76 to 32.28 | 54.11 to 57.49 | 87.12 to 90.02 |
| Nebulizer D: 5.18 to 5.21 μm (av 5.19) | 24.02 to 24.53 | 47.62 to 48.01 | 85.94 to 86.04 |

Overall average and standard deviation for MMD for all nebulisers for all runs: 4.73±0.32 μm
Approximately 30% of particles were ≤3 μm diam

| Nebulizer | Date | I: Vaccine nebulised gm (=mL) gm before − gm after | II: Vaccine Output (Rate) mL/min l/run time | III: Vaccine Nebulised (Rate) pfu/min $10^4$ × II | IV: Vaccine Conc'n pfu/L III/flow |
|---|---|---|---|---|---|
| A | May 27, 2003 | 99.99 − 98.14 = 1.85 | 1.85/4 = 0.463 | $10^4$ × 0.463 = 4.63 × $10^3$ | 4.63 × $10^3$/9.4 = 492 |
|   | May 29, 2003 | 56.97 − 55.71 = 1.26 | 1.26/2.43 = 0.518 | $10^4$ × 0.518 = 5.18 × $10^3$ | 5.18 × $10^3$/10.2 = 508 |
|   | Nov. 25, 2003* | 66.56 − 64.69 = 1.87 | 1.87/5 = 0.37 | $10^4$ × 0.37 = 3.7 × $10^3$ | 3.7 × $10^3$/10.2 = 363 |
|   | Nov. 25, 2003* | 66.75 − 64.86 = 1.89 | 1.89/5 = 0.378 | $10^4$ × 0.378 = 3.78 × $10^3$ | 3.78 × $10^3$/10.2 = 363 |
|   | Nov. 25, 2003* | 67.04 − 65.02 = 2.02 | 2.02/5 = 0.404 | $10^4$ × 0.404 = 4.04 × $10^3$ | 4.04 × $10^3$/10.2 = 371 |
| B | May 28, 2003 | 46.93 − 45.29 = 1.64 | 1.64/4 = 0.41 | $10^4$ × 0.41 = 4.1 × $10^3$ | 4.1 × $10^3$/9.4 = 436 |
|   | May 29, 2003 | 57.15 − 55.61 = 1.54 | 1.54/3.5 = 0.44 | $10^4$ × 0.44 = 4.4 × $10^3$ | 4.4 × $10^3$/10.7 = 411 |
|   | Nov. 26, 2003* | 66.48 − 64.71 = 1.77 | 1.77/5 = 0.354 | $10^4$ × 0.354 = 3.54 × $10^3$ | 3.54 × $10^3$/10.7 = 331 |
|   | Nov. 26, 2003* | 67.16 − 65.53 = 1.63 | 1.63/5 = 0.326 | $10^4$ × 0.326 = 3.26 × $10^3$ | 3.26 × $10^3$/10.7 = 305 |
|   | Nov. 26, 2003* | 68.21 − 66.44 = 1.77 | 1.77/5 = 0.354 | $10^4$ × 0.354 = 3.54 × $10^3$ | 3.54 × $10^3$/10.7 = 331 |
| C | May 28, 2003 | 47.11 − 45.8 = 1.31 | 1.31/4 = 0.328 | $10^4$ × 0.328 = 3.28 × $10^3$ | 3.28 × $10^3$/9.4 = 348 |
|   | May 29, 2003 | 57.54 − 56.05 = 1.49 | 1.49/3.5 = 0.425 | $10^4$ × 0.425 = 4.25 × $10^3$ | 4.25 × $10^3$/10.0 = 425 |
|   | Feb. 12, 2004* | 66.09 − 64.48 = 1.61 | 1.61/5 = 0.322 | $10^4$ × 0.322 = 3.22 × $10^3$ | 3.22 × $10^3$/10.0 = 322 |
|   | Feb. 12, 2004* | 66.34 − 64.69 = 1.65 | 1.65/5 = 0.33 | $10^4$ × 0.33 = 3.3 × $10^3$ | 3.3 × $10^3$/10.0 = 330 |
|   | Feb. 12, 2004* | 66.99 − 65.37 = 1.62 | 1.62/5 = 0.324 | $10^4$ × 0.324 = 3.24 × $10^3$ | 3.24 × $10^3$/10.0 = 324 |
| D | Feb. 17, 2004* | 66.03 − 64.35 = 1.68 | 1.68/5 = 0.336 | $10^4$ × 0.336 = 3.36 × $10^3$ | 3.36 × $10^3$/10.7 = 314 |
|   | Feb. 17, 2004* | 66.11 − 64.34 = 1.77 | 1.77/5 = 0.354 | $10^4$ × 0.354 = 3.54 × $10^3$ | 3.54 × $10^3$/10.7 = 331 |
|   | Feb. 17, 2004* | 67.16 − 65.17 = 1.99 | 1.99/5 = 0.398 | $10^4$ × 0.398 = 3.98 × $10^3$ | 3.98 × $10^3$/10.7 = 372 |

*20 L/min concentric supplemental air added to nebuliser outflow.

Theoretical vaccine concentration (pfu/L) emitted at the delivery end of the corrugated spacer tube:

|   | Malvern (approx 10 L/min Nebulizer flow) | Malvern with Supplemental Flow (Nebulizer flow + approx 20 L/min Supplemental flow at end of corrugated tubing) |
|---|---|---|
| Nebulizer A | 500 pfu/L | 377 pfu/L |
| Nebulizer B: | 424 pfu/L | 322 pfu/L |
| Nebulizer C: | 387 pfu/L | 325 pfu/L |
| Nebulizer D: | ND | 339 pfu/L |

Overall average and standard deviation for all nebulisers for all runs were calculated to be: average 437±58 pfu/L for 10 L/minute airflow and 341±25 pfu/L for supplemented airflow.

MMD: Mass Median Diameter in im

The MMD is automatically calculated by the Malvern Mastersizer X computer programme (see results in tables 4.1 to 4.3). A printout (see FIG. X) lists the parameters, date and time of the study and a graph giving the % of particles of diameters from 0.1 to 25 μm. In addition the cumulative % of the particles of each size is also printed.

Approximately 50% of particles were ≤5 μm diam
Greater than 85% of particles were ≤10 μm diam
Evaluation of Results.
Laser Setting:
  The records show that all runs were in the accepted % obscuration range of 5%-30%.
Compressor Settings:
  The records show that the pressure and air flow output of the compressor during all of the runs when fixed at the 40 psi setting were consistent. The pressure values ranged from 46.2 to 46.9 psi, and the air flow from 10.0 to 10.7 L/min.
Osmolarity.
  The increase in osmolarity of a solution remaining in the nebuliser after a run is an indication of whether there have been evaporative losses of the solution from the entry of dry gases into the nebuliser. The losses observed for the vaccine are not significant (eg <5%), but imply some slight concentration of the excipients. The lack of evaporative losses is because the Evans compressor compresses the ambient water vapor to pressures greater than the saturation point, thereby producing a "wet" gas driving the nebuliser.
Reproducibility:
  The results obtained for the individual nebulisers demonstrated that equivalent values for all parameters measured were obtained from separate runs on the same day, different runs on different days, with and without supplemental air flow, or from separate time readings during a single run. Cleaning and reuse did not show any effect on the results.

Robustness:

Neither the addition of 20 L concentric airflow at the corrugated spacer outflow, nor the somewhat lower pressure and airflow for the initial trial experiments caused changes to the particle size or distribution.

Nebulizer to Nebuliser Consistency:

There were minor differences in the measurements using the 4 different nebulisers. Nebulizer D had a slightly higher MMD.

Determination of the Vaccine Concentration in the Outflow of the Nebuliser:

At the settings used in the Mexican study (approx. 10 L/min, and pressure approx. 47 psi—with no supplemental airflow) the theoretical vaccine concentration was calculated to be approximately 437 pfu/L.

Conclusions.

The experiments on the Mexican Device (IPI nebuliser and Evans Compressor) at the settings used in the Mexican clinical trials, using the Malvern Mastersizer X laser particle demonstrated that the output of measles vaccine nebulised by the Mexican device is consistent and reproducible.

The data obtained is of satisfactory quality to be used for the comparative assessment of other nebuliser/compressor aerosol devices to demonstrate that these other devices with potentially more suitable characteristics, have equivalent output for all parameters measured and calculated for the Mexican device.

Further experimentation was then carried out on the Mexican Device using different conditions to further characterise the preferred particle sizes and conditions to be used by candidate devices.

Animal Studies

A single dose animal study was carried out with measles aerosol vaccines including the SIIL EZ measles vaccine. This were performed on behalf of WHO with parenteral vaccine administration as the control.

The study studied both safety and efficacy in Macaque monkeys that are susceptible to measles vaccine infection and therefore a suitable animal model for both safety and efficacy. The animals for safety were treated with immunosuppressants to give a "worst case" where animals would be more susceptible to infection by the live vaccine virus, and therefore more likely to suffer any measles specific adverse events.

The parameters studies for safety were: characterization of immune suppression; hematology; BAL cell phenotyping; vaccine virus isolation; serology; and necropsy blood and tissue examination. This single dose safety study in immunosuppressed non-human primates, showed no evidence of a safety problem associated with aerosol measles vaccination in comparison with parenteral vaccination.

The parameters evaluated for the efficacy study were: hematology; BAL cell phenotyping; vaccine virus isolation; vaccine virus detection by PCR; serology; cell mediated immunity. The immunogenicity and protective capacity to a challenge dose of measles of the EZ vaccine administered by jet nebuliser or by injection was comparable. The level of protection produced to measles virus challenge was similar in all immunized groups. In conclusion, these studies confirmed the efficacy of measles vaccinations via the aerosol route.

A GLP toxicology study in non-human primates was performed to evaluate the potential toxicity of Edmonston-Zagreb Measles Vaccine produced by the Serum Institute of India following two administrations by inhalation to cynomolgous monkeys (Macaque). Two nebulisers were used, one which supplies predominantly low droplet size (median mass diameter MMD 1-5 uM) particles (Mexican classical device) and one which supplies predominantly high droplet size (MMD 10 uM) particles. In this way, the study covers the toxicity of a range of particle sizes in order to encompass those that may be encountered in clinical use.

All aspects of this study were planned in compliance with international good laboratory practice regulations and guidelines, and with the EU Animal Health regulation (November 1986).

One dose of measles vaccine given to infants of 9-12 months is expected to give lifelong immunity, but many children receive a second dose on school entry, or during mass campaigns. This two-dose study was designed to give adequate toxicity information for two doses of measles vaccine by aerosol. The non-human primate model was chosen as the most suitable animal model for toxicity studies. Forty eight monkeys were included in the study in 4 groups, each with 6 animals of each sex. The animals were subjected to vaccine or placebo (excipients) at approximately 5 times the human daily dose.

All animals received the first dose of vaccine or placebo (excipients) on day 0. At day 7, when measles viremia is expected to be at a peak, half of the animals/sex/group were sacrificed for analysis of toxicity. The remaining animals received a second dose on day 21, and were sacrificed on day 42. As these animals are expected to be protected by the initial dose by day 21, the 21-day recovery time after the second dose was chosen to provide an indication of any delayed or prolonged toxicity to two doses of vaccine. The choice of placebo was made to determine the potential toxicity of the excipients as well as from the measles virus by inhalation.

The results of the study showed no toxic effects related to the vaccine or placebo.

Initial results indicated that there was little difference in toxicity between the lower droplet size and the higher droplet size. However, utilising a piezoelectric device such as a vibrating element nebuliser was seen to improve vaccine potency retention. This considerably improves the use of such devices in the field, as ice for keeping the devices cold is not required.

Additionally, initial results have indicated that it should be possible to provide one dose for all age groups between the age of twelve months and 18 years for children. The estimated volume of the dose will be 0.25 ml, with the time to deliver each dose adapted for different devices.

Suitable Nebulisers Include:

1. The CompAir Elite, NE-C21 portable handheld compressor/nebuliser manufactured by OMRON Healthcare Inc., Ill.
2. Another suitable nebuliser is the Aeroneb Pro™, available from Nektar Inc. This latter device utilises a piezoelectric delivery system in the nebuliser.

From these initial results and from the experience of the Applicants, it has been possible to identify a preferred combination of features to allow a nebuliser to be produced that is suitable for use by multiple patients within the field. For example, for use in tropical or remote regions.

The nebuliser ideally is supportable in a hand, that is, it is hand held.

Figure 1:
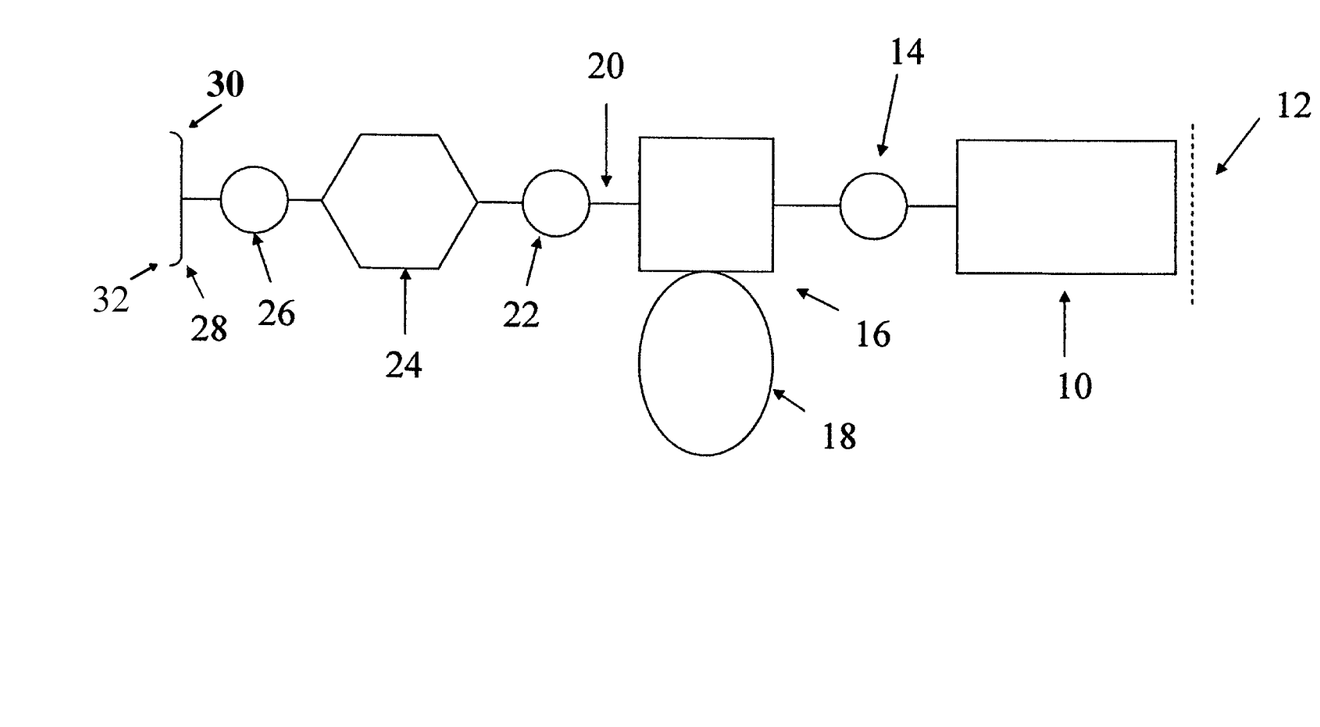
FIG. 1 shows a schematic diagram indicating the general arrangement of a nebuliser according to the invention.

The FIG. 1 shows a schematic representation of the arrangement of a nebuliser according to the invention. The nebuliser preferably comprises a compressor (10). However, other ways of propelling the aerosol into the lungs, such as using the flow of air provided by the patient may also be used. The inlet of the compressor comprises a filter to reduce the amount of intake of pathogens into the compressor. The filter is indicated as 12 on the schematic diagram. The compressor is attached to a nebuliser via a one-way valve (14). This prevents back-flow of contaminated air into the compressor (10). The nebuliser element (16) comprises the components making the aerosol. As already indicated, such nebulisers, including jet nebulisers and piezoelectric nebulisers, are known. The nebuliser (16) additionally comprises a receptacle (18) for receiving the vaccine. The nebuliser may then be connected to a flexible tubing made of any suitable material such as plastic tubing (20). A one-way valve (22) may be provided to prevent the return of air into the nebuliser. Attached to the one-way valve may be provided a spacer (24). The spacer may in turn be attached, by an optional one-way valve (26), to a suitable face mask (28), mouthpiece (30) or nasal prongs (32).

The individual components of the invention are themselves known. However, the invention allows the optimisation of the nebuliser system.

Preferably, the source of energy is a rechargeable battery, rather than mains electricity. The advantage of using a rechargeable battery is that the device can be used remote from mains electricity. Furthermore, a rechargeable battery may be recharged using, for example, solar energy, so avoiding the requirement to have a generator or mains electricity available.

We claim:

1. A method for administering a vaccine, the method comprising the steps of:
   providing a vaccine;
   combining the vaccine with at least one nebuliser device, wherein the at least one nebuliser device produces a plurality of vaccine particles from the vaccine;
   using a particle size analyzer to measure a particle droplet size distribution of the plurality of vaccine particles produced from the at least one nebuliser device;
   administering the plurality of vaccine particles from the at least one nebuliser device to a patient, wherein the plurality of vaccine particles have the following particle droplet size distribution:
   (i) $D_{v10}$: 2.0+/−0.2 μm
   (ii) $D_{v50}$: 5.0+/−0.5 μm
   (iii) $D_{v90}$: 10.0+/−1.0 μm
   (iv) a mean mass aerodynamic diameter (MMAD) having a range with a lower limit above 5.0 μm and an upper limit at 8.0 μm.

2. The method of claim 1, wherein the particle droplet size distribution has a mean mass aerodynamic diameter (MMAD) of 6.5 μm with a Geometric Standard Deviation (GSD) of 1.7.

3. The method of claim 1, wherein the step of identifying a nebuliser device further requires that the identified nebuliser device allows a potency retention of at least about 75% for a reconstituted vaccine delivered by the nebuliser device to a patient after 40 doses have been delivered.

4. The method of claim 3, wherein the step of identifying a nebuliser device requires that the reconstituted vaccine comprises an Edmonston-Zagreb vaccine.

5. The method of claim 1, wherein the step of identifying a nebuliser device further requires that the nebuliser device comprise a receptacle for receiving two or more doses of vaccine.

6. The method of claim 1, wherein the step of identifying a nebuliser device further requires that the nebuliser device be able to produce a substantially consistent dose delivery for each delivery of the virus.

7. The method of claim 1, wherein the step of identifying a nebuliser device further requires that the identified nebuliser device be capable of delivering vaccine particles, wherein at least about 95% of the particles are greater than about 0.5 μm in diameter (MMAD).

8. The method of claim 3, wherein the potency retention is achieved without cooling the reconstituted vaccine.

9. The method of claim 1, wherein the method further comprises:
   screening the nebuliser device for the ability to provide an immunizing dose of vaccine to an infant or child within 20 to 40 seconds.

10. The method of claim 4, wherein the method further comprises the step of requiring a receptacle for receiving the two or more doses of vaccine, whereby the receptacle is detachable, and whereby the receptacle provides an environment suitable to prevent contamination of the vaccine within the receptacle.

11. The method of claim 10, whereby the receptacle containing the vaccine provides the environment suitable to prevent contamination of the vaccine between vaccinations.

12. The method of claim 1, further comprising the step of requiring the nebuliser device to comprise a piezoelectric nebulising element.

13. The method of claim 1, further comprising the step of requiring the nebuliser device to comprise an air delivery element.

14. The method of claim 13, wherein the air delivery element comprises an air intake filter operable to filter airborne microorganisms.

15. The method of claim 1, further comprising the step of requiring the nebuliser device to comprise a facial interface, adapted to substantially fit the contours of a patient's face when in use.

16. The method of claim 15, further comprising the step of requiring a nebuliser element in fluid connection with the facial interface, a mouthpiece, or nasal prongs via a spacer.

17. The method of claim 16, further comprising the step of requiring the nebuliser device to comprise one or more air hoses between the facial interface, the mouthpiece, or the nasal prongs and the nebuliser element.

18. The method of claim 17, further comprising the step of requiring one or more of a receptacle, the nebuliser element, the facial interface, the mouthpiece, the nasal prongs, an air intake filter, or the air hose to be disposable.

19. The method of claim 18, wherein the nebuliser device further comprises a one-way valve between a patient utilizing the nebuliser device, and one or more of a nebuliser element, and an air delivery means when used.

20. The method of claim 19, wherein the nebuliser device further comprises a needle-free vaccine loading device.

21. A method for administering a vaccine, the method comprising the steps of:
   providing a vaccine;
   combining the vaccine with at least nebuliser device, wherein the at least one nebuliser device produces vaccine particles from the vaccine;
   measuring a particle droplet size distribution of the vaccine particles produced from the at least one nebuliser device using a particle size analyzer;
   administering the plurality of vaccine particles from the at least one nebuliser device to a patient, wherein the nebuliser device comprises:
   a piezoelectric nebulising element that nebulizes the vaccine such that the plurality of vaccine particles that are administered to the patient display the following particle droplet size distribution:
   (i) $D_{v10}$: 2.0+/−0.2 μm
   (ii) $D_{v50}$: 5.0+/−0.5 μm (iii) $D_{v90}$: 10.0+/−1.0 µm (iv) a mean mass aerodynamic diameter (MMAD) having a range with a lower limit above 5.0 µm and an upper limit at 8.0 µm and at least one element selected from the group consisting of:

(a) an air intake filter capable of filtering airborne microorganisms;

(b) a facial interface adapted to fit substantially to the contours of the face of a patient;

(c) one or more connections for receiving a supply of vaccine, wherein the connections are selected from the group consisting of a mouthpiece, a nasal prong, and an air hose; and (d) a receptacle for receiving a two or more doses of vaccine;

wherein the nebulising element and the at least one element are operably connected to one another.

22. The method of claim 21, whereby the nebuliser device comprise at least two different elements selected from the group identified in claim 21.

23. The method of claim 21, whereby the nebuliser device comprise at least three different elements selected from the group identified in claim 21.

24. A method for administering a vaccine, the method comprising the steps of:

providing a vaccine;

combining the vaccine with at least one nebuliser device, wherein the at least one nebuliser device produces vaccine particles from the vaccine;

measuring a particle droplet size distribution of the vaccine particles from the at least one nebuliser device using a particle size analyzer;

administering the plurality of vaccine particles from the at least one nebuliser device to a patient, wherein the nebuliser devise comprises:

(a) a piezoelectric nebulising element that nebulizes the vaccine such that the plurality of vaccine particles that are administered to the patient display the following particle droplet size distribution:

(i) $D_{v10}$: 2.0+/−0.2 µm (ii) $D_{v50}$: 5.0+/−0.5 µm (iii) $D_{v90}$: 10.0+/−1.0 µm (iv) a mean mass aerodynamic diameter (MMAD) having a range with a lower limit above 5.0 µm and an upper limit at 8.0 µm (b) an air intake filter capable of filtering airborne microorganisms;

(c) a facial interface adapted to fit substantially to the contours of the face of a patient;

(d) one or more connections for receiving a supply of vaccine, wherein the connections are selected from the group consisting of a mouthpiece, a nasal prong, and an air hose; and (e) a receptacle for receiving a two or more doses of vaccine;

wherein the nebulising element, the air intake filter, the facial interface, the one or more connection for receiving a supply of vaccine, and the receptacle are operably connected to one another.

25. The method of claim 24, whereby the nebuliser device further comprises a rechargeable battery.

26. The method of claim 25, whereby the nebuliser device further comprises a needle-free vaccine loading device.

27. The method of claim 21, wherein the vaccine is administered as an aerosol via the nebuliser device.

\* \* \* \* \*